US012478471B2

(12) United States Patent
Wu et al.

(10) Patent No.: US 12,478,471 B2
(45) Date of Patent: Nov. 25, 2025

(54) MEDICAL IMPLANT CONVEYING DEVICE

(71) Applicant: SHANGHAI MICROPORT CARDIOFLOW MEDTECH CO., LTD., Shanghai (CN)

(72) Inventors: Xuwen Wu, Shanghai (CN); Jie Mei, Shanghai (CN); Baozhu Gui, Shanghai (CN); Guoming Chen, Shanghai (CN); Yu Li, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 961 days.

(21) Appl. No.: 17/634,386

(22) PCT Filed: Aug. 24, 2020

(86) PCT No.: PCT/CN2020/110893
§ 371 (c)(1),
(2) Date: Feb. 10, 2022

(87) PCT Pub. No.: WO2021/043022
PCT Pub. Date: Mar. 11, 2021

(65) Prior Publication Data

US 2022/0323216 A1 Oct. 13, 2022

(30) Foreign Application Priority Data

Sep. 3, 2019 (CN) ........................ 201910829483.9

(51) Int. Cl.
*A61F 2/24* (2006.01)
*A61F 2/95* (2013.01)
(Continued)

(52) U.S. Cl.
CPC .......... *A61F 2/2436* (2013.01); *A61F 2/9517* (2020.05); *A61F 2/962* (2013.01); *A61F 2/966* (2013.01)

(58) Field of Classification Search
CPC .................. A61F 2/2436; A61F 2/9517; A61F 2/2427–2439; A61F 2/95–97;
(Continued)

(56) References Cited

U.S. PATENT DOCUMENTS

2003/0153941 A1 8/2003 Rourke
2008/0097572 A1 4/2008 Sheldon et al.
2013/0211494 A1 8/2013 Snow et al.
2014/0135734 A1* 5/2014 Dakin ............... A61M 25/0082 604/93.01
(Continued)

FOREIGN PATENT DOCUMENTS

CN 107496055 A 12/2017
CN 208974214 U 6/2019
(Continued)

*Primary Examiner* — Sarah W Aleman
*Assistant Examiner* — Mikail A Mannan
(74) *Attorney, Agent, or Firm* — MUNCY, GEISSLER, OLDS & LOWE, P.C.

(57) ABSTRACT

The present invention provides a delivery device for medical implants. The delivery device has a detachable structure and includes a handle (3) and a catheter assembly (1) that are separated from each other. The handle (3) and the catheter assembly (1) are connected by a transmission shaft (2). By configuring the handle (3) and the catheter assembly (1) to be separated from each other, the catheter assembly (1) has less weight than that of a traditional delivery assembly, so that the operator can position the medical implant and adjust the position of the medical implant by moving only the catheter assembly (1). The catheter assembly (1) is lighter in weight and smaller in size, which improves the stability, precision and accuracy of the operation. Moreover, the impact of vibration and/or movement of the handle (3) on
(Continued)

the catheter assembly (1) are avoided, which further improves the stability and thus the quality of the operation.

16 Claims, 6 Drawing Sheets

(51) Int. Cl.
*A61F 2/962* (2013.01)
*A61F 2/966* (2013.01)

(58) Field of Classification Search
CPC ........ A61F 2220/0041; A61F 2250/006; A61F 2/962; A61F 2/966; A61M 25/0136; A61B 2017/0046; A61B 2017/00477
See application file for complete search history.

(56) References Cited

U.S. PATENT DOCUMENTS

| | | | | |
|---|---|---|---|---|
| 2015/0025621 | A1* | 1/2015 | Costello | A61F 2/2436 623/2.11 |
| 2015/0057738 | A1 | 2/2015 | Hepke et al. | |
| 2015/0073539 | A1 | 3/2015 | Geiger et al. | |
| 2015/0282964 | A1 | 10/2015 | Beard et al. | |
| 2017/0340877 | A1* | 11/2017 | Ollivier | A61N 1/3756 |

FOREIGN PATENT DOCUMENTS

| | | | | |
|---|---|---|---|---|
| CN | 211156474 | U | 8/2020 | |
| JP | 2010527695 | A | 8/2010 | |
| JP | 2014513585 | A | 6/2014 | |
| KR | 1020150125240 | A | 11/2015 | |
| WO | WO-2019/023258 | A1 | 1/2019 | |
| WO | WO-2019147504 | A1 * | 8/2019 | A61F 2/2436 |

* cited by examiner

MEDICAL IMPLANT CONVEYING DEVICE

TECHNICAL FIELD

The present invention relates to the technical field of medical surgical device and, more specifically, to a delivery device for medical implants.

BACKGROUND

The transapical approach is a common approach for cardiac surgery. The incision on the body surface is very close to the target valve (i.e., the distance therebetween is about 10 cm or less). The incision, the point for heart puncturing and the center of the valve ring are of good coaxiality. Therefore, a delivery device is usually designed to have an overall rigid straight tube so as to allow the operator to be able to adjust the angle and the depth of the device in a more sensitive and intuitive way.

In TAVI (Transcatheter Aortic Valve Implantation), TMVR (Transcatheter Mitral Valve Replacement) and other valve replacement surgeries, transapical approach is applied. These replacement surgeries require high release accuracy. Real-time position maintenance and fine adjustment of position are required before release, during release, retrieval, and re-release of the prosthesis. The existing delivery device is large in size and heavy in weight, and thus the entire delivery device is relatively cumbersome and poor in stability when operated by human hands. Therefore, in surgery, the commonly used device positioning and stabilization method is to add a holding system to the delivery device in such a way that one end of the holding system is fixed at the operating table, and the other end clamps and holds the handle of the delivery device to meet the requirements with regard to positioning and stability of the delivery device during the operation.

However, the holding system is required to provide a stable supporting force and satisfy multiple degrees of freedom. Therefore, the holding system is usually heavy and bulky, which will prolong the duration of the operation to a certain extent for the reasons as follows:

1. There are many operating steps, involving the construction, adjustment and fastening of a holder and the like;
2. In an operation, the complexity in operating the holder may also have an influence on the duration of the operation;
3. The size of the holder is generally large, which adversely affects the convenience of other operations;

In view of the above shortcomings, a delivery device is needed that can adjust the position of the implant for release thereof according to requirements in real time, which makes it possible to not only accurately release the prosthesis to the target position, but also shorten the time consumed for adjusting the position of the delivery device as much as possible, thereby shortening the operation time and achieving a valve replacement with high quality.

SUMMARY OF THE INVENTION

An object of the present invention is to provide a delivery device for medical implants, which is conducive to the positioning and position adjustment of the medical implants, improves the operation precision and accuracy of the operation for medical implants, and improves the stability of the delivery device.

The present invention provides a delivery device for medical implants, wherein the delivery device has a detachable structure and includes a handle and a catheter assembly that are separated from each other, and the handle and the catheter assembly are connected by a transmission shaft.

Further, the transmission shaft is detachably connected to the catheter assembly.

Further, the catheter assembly comprises an inner tube assembly and an outer tube assembly sleeved over the inner tube assembly, and wherein the handle is configured to drive the transmission shaft to rotate to axially move the outer tube assembly relative to the inner tube assembly.

Further, the catheter assembly further comprises a transmission assembly, the transmission assembly comprising a screw rod and a screw nut, wherein the screw rod is engaged with the screw nut that is fixedly connected to the outer tube assembly; when the transmission shaft is connected to the catheter assembly, the transmission shaft is connected to the screw rod so that the screw nut and the outer tube assembly are forced to move axially resulting from rotation of the screw rod due to rotation of the transmission shaft.

Further, the catheter assembly further comprises a housing, and the transmission assembly further comprises a first bearing, and wherein an outer ring of the first bearing is embedded in and fixedly connected to a proximal end of the housing, and an inner ring of the first bearing is sleeved over and fixedly connected to a proximal end of the screw rod.

Further, the inner tube assembly comprises a tapered head, a distal inner tube, a fastener and a proximal inner tube that are sequentially connected along a direction from a distal end to a proximal end.

Further, the outer tube assembly comprises a sheath tube and a first outer tube connected to a proximal end of the sheath tube, and wherein the first outer tube has a proximal end fixedly connected to the screw nut.

Further, the first outer tube has an inner wall where a circumferential stopper is provided, and an outer wall of the proximal inner tube matches with the circumferential stopper so that the proximal inner tube is restricted from rotating circumferentially.

Further, the catheter assembly further comprises a first stabilizing tube having a proximal end fixedly connected to a distal end of the housing, and wherein the first stabilizing tube is sleeved over the first outer tube.

Further, the inner tube assembly further comprises an intermediate inner tube and a Luer connector having a protruding end, and wherein the tapered head, the distal inner tube, the fastener, the intermediate inner tube, the Luer connector, and the proximal inner tube are sequentially connected along a direction from a distal end to a proximal end.

Further, the transmission assembly further comprises two second bearings, and wherein a through hole is formed axially in the screw rod, and the proximal inner tube passes through and is in clearance fit with the through hole, each of the second bearings is sleeved over a respective one of two ends of the proximal inner tube, an outer ring of each of the second bearings is fixedly connected to an inner wall of a respective end of the screw rod, and an inner ring of the first bearing is sleeved over and fixedly connected to a proximal outer wall of the screw rod.

Further, the inner tube assembly comprises, along a direction from a distal end to a proximal end, a tapered head, a distal inner tube, a fastener, and a middle inner tube and a Luer connector having a protruding end.

Further, the outer tube assembly comprises a sheath tube and a second outer tube connected to a proximal end of the sheath tube, and wherein a proximal end of the second outer tube is fixedly connected to the screw nut; a first strip-shaped opening is axially defined on the second outer tube, and the protruding end of the Luer connector protrudes from the first strip-shaped opening.

Further, the catheter assembly further comprises a second stabilizing tube having a proximal end fixedly connected to a distal end of the housing, the second stabilizing tube is sleeved over the second outer tube, a second strip-shaped opening is axially defined on the second stabilizing tube, and the second strip-shaped opening is in positional correspondence with the first strip-shaped opening, the protruding end of the Luer connector protrudes from the first strip-shaped opening and then protrudes from the second strip-shaped opening.

Further, the catheter assembly further comprises a circumferential stop piece fixedly connected to the screw nut, and wherein the circumferential stop piece cooperates with the housing so that the outer tube assembly and the housing are circumferentially locked and axially movable.

Further, the transmission shaft comprises a flexible transmission shaft.

Further, the flexible transmission shaft has 2 to 4 layers of spiral structure, each of which has an outer diameter greater than or equal to 0.1 mm, and the flexible transmission shaft is made of metal.

Further, the transmission shaft further comprises a connector and an outer tube for the flexible transmission shaft, and wherein the outer tube for the flexible transmission shaft is sleeved over the flexible transmission shaft, and the flexible transmission shaft is connected to the catheter assembly by the connector.

Further, the transmission shaft is fixedly connected to the catheter assembly.

Compared to the prior art, the present invention offers the following advantages:

The delivery device for medical implants has a detachable structure and includes a handle and a catheter assembly that are separated from each other. Different from the traditional delivery system, the operator can position the medical implant and adjust the position of the medical implant by moving the catheter assembly having light weight and small size. Compared with the traditional delivery system which is only allowed to be moved integrally, the catheter assembly is lighter in weight and smaller in size, and can be moved more conveniently and flexibly. It is thus more conducive to the positioning and the fine-tuning of the position during the operation, and improves the stability, precision and accuracy of the operation. A high-quality implantation of medical implants can be achieved. Moreover, the impact of vibration and/or movement of the handle on the catheter assembly are avoided, which further improves the stability and thus the quality of the operation.

Further, the transmission shaft and the catheter assembly are detachably connected, which improves the convenience in the process of loading, transporting and releasing the medical implant, and the detachable connection also improves the convenience of packaging and transportation.

Further, the transmission shaft is flexible and can be wound so that the overall size of the packaged delivery device can be reduced and also the space occupied during surgery can be reduced.

Further, a through hole is defined in the screw rod in the axial direction, and the proximal inner tube passes through the through hole. Therefore, the space inside the screw rod is utilized skillfully, thereby reducing the size of the catheter assembly so that the catheter assembly is more compact, which makes it more suitable for holding, moving, and positioning.

LIST OF REFERENCE NUMERALS

1—catheter assembly; 2—transmission shaft; 3—handle; 11—outer tube assembly; 12—inner tube assembly;

13—housing; 14—transmission assembly; 111—sheath tube; 112—second outer tube; 113—screw nut; 114—circumferential stop piece; 115—first outer tube; 121—tapered head; 122—distal inner tube; 123—fastener; 124—middle inner tube; 125—Luer connector; 126—proximal inner tube; 133—housing lining; 141—retaining nut for inner tube; 142—second bearing; 143—seat for screw rod; 144—screw rod; 145—seat for flexible shaft; 146—first bearing; 15—second stabilizing tube 21—flexible transmission shaft; 22—connector; 23—outer tube for flexible transmission shaft; 241—first fastener; 242—second fastener.

DETAILED DESCRIPTION

An embodiment of the present invention provides a delivery device for medical implant. The present invention will be described in greater detail below with reference to specific embodiments which are to be read in conjunction with the accompanying drawings. Advantages and features of the present invention will be apparent from the description below. It is noted that the figures are provided in a very simplified form not necessarily presented to scale, with their only intention to facilitate convenience and clarity in explaining the disclosed embodiments.

Figure 1:
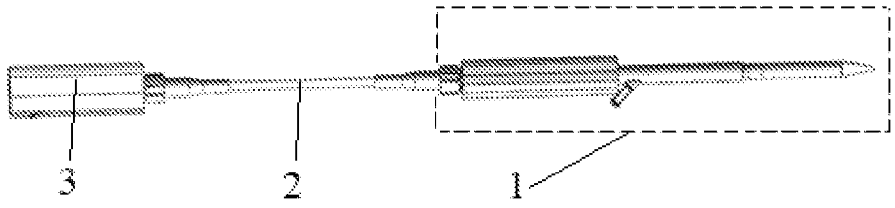
FIG. 1 is a schematic diagram showing the structure of a delivery device for medical implant according to an embodiment of the present invention.

FIG. 1 is a schematic diagram showing the structure of a delivery device for medical implant according to an embodiment of the present invention. As shown in FIG. 1, an embodiment of the present invention provides a delivery device for medical implant. The delivery device is detachable and includes: a handle 3 and a catheter assembly 1 that are separated from each other, and the handle 3 and the catheter assembly 1 are connected by a transmission shaft 2. Since the handle 3 and the catheter assembly 1 are separated from each other, the handle 3 and the catheter assembly 1 are not arranged in a same housing, and they are independent from each other. Each of the handle 3 and the catheter assembly 1 is housed by its own housing and has its own components inside it. The transmission shaft 2 can be detachably or fixedly connected with the catheter assembly 1, where the connection therebetween can be selected according to actual needs. Specifically, the catheter assembly 1 includes an inner tube assembly and an outer tube assembly sleeved over the inner tube assembly. The handle 3 drives the transmission shaft 2 to rotate so that the outer tube assembly is movable relative to the inner tube assembly along the axial direction thereof. Hereinafter, the term “distal” refers to a side closer to the catheter assembly 1, while the term “proximal” refers to a side closer to the handle 3. The outer tube assembly and the inner tube assembly are coaxial. The axial direction herein refers to a direction parallel to the axis of the outer tube assembly (or inner tube assembly), and the circumferential direction refers to a direction along the circumference in a plane perpendicular to the axial direction.

The catheter assembly 1 is used for loading, transporting and releasing medical implants. The transmission shaft 2 is used for transmitting the movement signal from the handle 3 to the catheter assembly 1 during the stages of loading, releasing and retrieving the medical implants. The handle 3 is used to provide power during the stages of loading, releasing, and retrieving medical implants, and to control the catheter assembly 1 through the transmission shaft 2.

In this embodiment, the delivery device for medical implant has a detachable structure and includes a handle 3 and a catheter assembly 1 that are separated from each other. The operator can position the medical implant and adjust the position of the medical implant by moving only the catheter assembly 1. Compared with the traditional delivery system which is only allowed to be moved integrally, the catheter assembly is lighter in weight and smaller in size, and can be moved more conveniently and flexibly. It is thus more conducive to the positioning and the fine-tuning of the position during the operation, and improves the stability, precision and accuracy of the operation. A high-quality implantation of medical implants can be achieved. Moreover, the impact of vibration and/or movement of the handle on the catheter assembly are avoided, which further improves the stability and thus the quality of the operation.

The transmission shaft 2 and the catheter assembly 1 are detachably connected, so that the transmission shaft 2 and the catheter assembly 1 can be disconnected from or connected with each other according to requirements. Specifically, when the medical implant is loaded in vitro, the transmission shaft 2 and the catheter assembly 1 are connected; after the medical implant is loaded, the transmission shaft 2 and the catheter assembly 1 are disconnected just before the medical implant is released at the diseased location. The catheter assembly 1 is used alone, which is more conducive to the positioning and the fine-tuning of position, thereby improving the accuracy and stability; when the medical implant is released or retrieved, the transmission shaft 2 and the catheter assembly 1 are connected again, and the release or retrieval of the medical implant can be achieved by operating the control handle 3. Moreover, the detachable connection between the transmission shaft 2 and the catheter assembly 1 improves the convenience of packaging and transportation. In addition, the transmission shaft 2 and the handle 3 do not directly contact human tissues, and can be reused, thereby saving resources.

Figure 2:
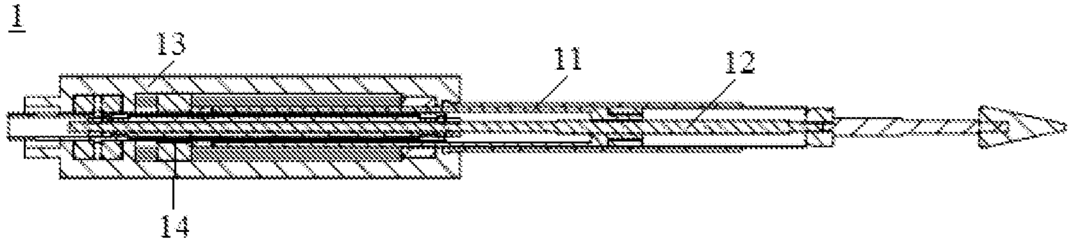
FIG. 2 is a cross-sectional view of a first exemplary catheter assembly according an embodiment of the present invention.

FIG. 2 is a cross-sectional view of a first exemplary catheter assembly according an embodiment of the present invention. As shown in FIGS. 1 and 2, the catheter assembly 1 includes an outer tube assembly 11, an inner tube assembly 12, a housing 13 and a transmission assembly 14. The outer tube assembly 11 is sleeved over the inner tube assembly 12, and the transmission assembly 14 is arranged inside the housing 13. In this embodiment, the inner tube assembly 12 and the housing 13 are relatively stationary with each other, and the outer tube assembly 11 is driven by the handle 3 to move axially relative to the inner tube assembly 12.

Figure 3:
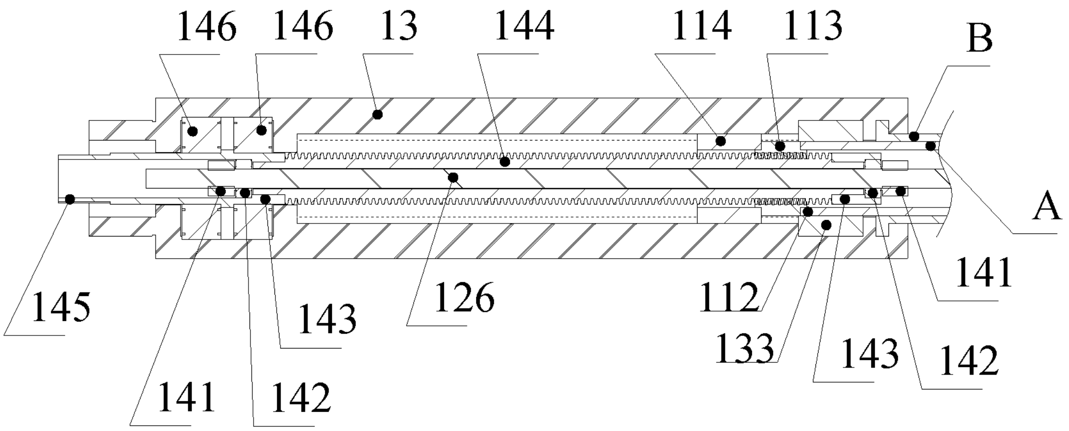
FIG. 3 is an enlarged view of part of the proximal end of the catheter assembly according to an embodiment of the present invention.

FIG. 3 is an enlarged view of part of the proximal end of the catheter assembly according to an embodiment of the present invention. As shown in FIGS. 1 to 3, the transmission assembly 14 includes a screw rod 144, a screw nut 113, and a first bearing 146. The outer ring of the first bearing 146 is embedded and fixed in the proximal end of the housing 13. The inner ring of the first bearing 146 is sleeved and fixed on the proximal end of the screw rod 144. The screw rod 144 is engaged with the screw nut 113. The screw nut 113 is fixedly connected to the outer tube assembly 11. When the transmission shaft is connected with the catheter assembly, the transmission shaft 2 is fixedly connected to the screw rod 144 so that the rotation of the transmission shaft 2 may cause the rotation of the screw rod 144, and thus the screw nut 113 and the outer tube assembly 11 are accordingly forced to move axially.

Figure 4:
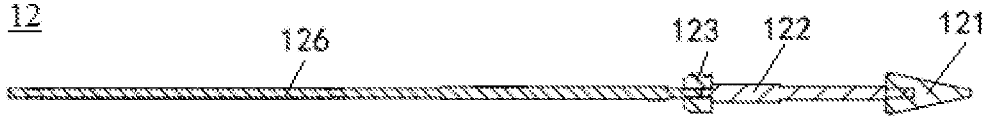
FIG. 4 is a schematic diagram showing the structure of a first exemplary inner tube assembly (excluding the Luer connector) according to an embodiment of the present invention.
Figure 5:
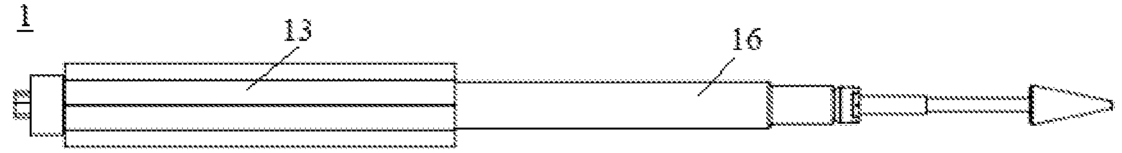
FIG. 5 is a schematic diagram showing the structure of the first exemplary catheter assembly according an embodiment of the present invention.
Figure 6:
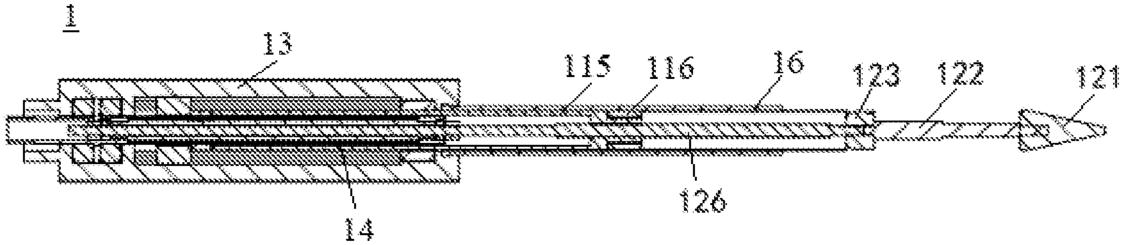
FIG. 6 is a cross-sectional view of FIG. 5.
Figure 7:
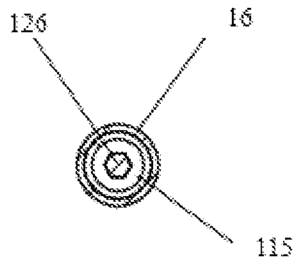
FIG. 7 is a cross-sectional view of the circumferential stopper shown in FIG. 6.

FIG. 4 is a schematic diagram showing the structure of a first exemplary inner tube assembly (excluding the Luer connector) according to an embodiment of the present invention. FIG. 5 is a schematic diagram showing the structure of the first exemplary catheter assembly according an embodiment of the present invention. FIG. 6 is a cross-sectional view of FIG. 5. FIG. 7 is a cross-sectional view of the circumferential stopper shown in FIG. 6. As shown in FIGS. 4 to 7, along a direction from the distal end to the proximal end, the inner tube assembly 12 includes: a tapered head 121, a distal inner tube 122, a fastener 123, and a proximal inner tube 126 that are connected in sequence. The outer tube assembly includes a sheath tube and a first outer tube 115 connected to the proximal end of the sheath tube. The proximal end of the first outer tube 115 is fixedly connected to the screw nut. The inner wall of the first outer tube 115 is provided with a circumferential stopper 116, and the outer wall of the proximal inner tube 126 matches the circumferential stopper 116 so that the circumferential rotation of the proximal inner tube 126 is prevented. The catheter assembly 1 further includes a first stabilizing tube 16 having a proximal end fixedly connected to the distal end of the housing 13, and the first stabilizing tube 16 is sleeved over the first outer tube 115. The inner tube assembly of this embodiment may be a solid tube, which may be integrally formed, or may be separately manufactured and then connected by welding or bonding. Therefore, the processing and manufacturing are more convenient. A design for emptying the outer tube can be applied according to actual needs.

Figure 8:
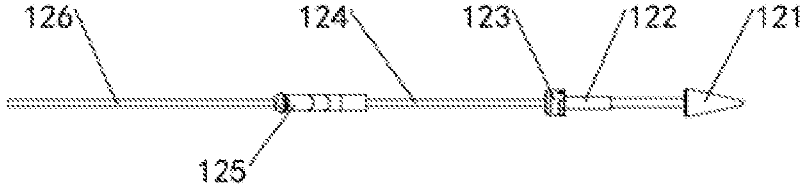
FIG. 8 is a schematic diagrams showing the structure of a second exemplary inner tube assembly (including a proximal inner tube and a Luer connector) according an embodiment of the present invention.
Figure 9:
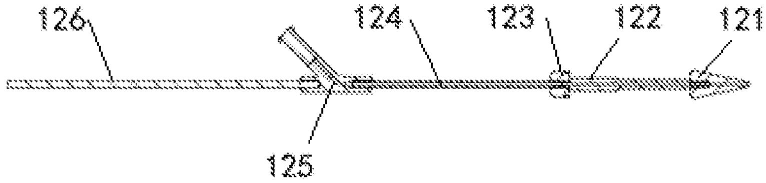
FIG. 9 is a cross-sectional view of FIG. 8.
Figure 10:
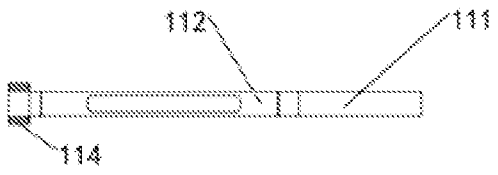
FIG. 10 is a front view of an outer tube assembly according to an embodiment of the present application.
Figure 11:
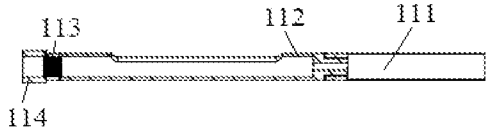
FIG. 11 is a cross-sectional view of FIG. 10.

FIG. 8 is a schematic diagrams showing the structure of a second exemplary inner tube assembly (including a proximal inner tube and a Luer connector) according an embodiment of the present invention. FIG. 9 is a cross-sectional view of FIG. 8. FIG. 10 is a front view of an outer tube assembly according to an embodiment of the present application. FIG. 11 is a cross-sectional view of FIG. 10.

As shown in FIGS. 8 and 9, the inner tube assembly further includes a middle inner tube 124 and a Luer connector 125. The Luer connector 125 has a protruding end. The tapered head 121, the distal inner tube 122, the fastener 123, the middle inner tube 124, the Luer connector 125, and the proximal inner tube 126 are fixedly connected in sequence along a direction from the distal end to the proximal end. As shown in FIGS. 9 to 11, the outer tube assembly includes: a sheath tube 111, a second outer tube 112 fixedly connected to the proximal end of the sheath tube 111, and the proximal end of the second outer tube 112 is fixedly connected to the screw nut 113. The second outer tube 112 has a first strip-shaped opening along the axial direction thereof. The sheath tube 111 is used to cover the medical implant sleeved on the distal inner tube 122.

As shown in FIGS. 3, 4 and 9, in both the structures of the two exemplary inner tube assemblies shown in FIGS. 4 and 9, the proximal inner tube 126 is included, and the proximal inner tube 126 can be placed inside the screw rod 144 so that the axial position of the proximal inner tube 126 can be limited through using the screw rod 144, and thus the axial position of the inner tube assembly can be limited. According to the embodiment, the space inside the screw rod 144 is utilized skillfully, thereby reducing the size of the catheter assembly 1 so that the catheter assembly 1 is more compact, which makes it more suitable for holding, moving, and positioning.

As shown in FIG. 3, the transmission assembly 14 not only includes the screw rod 144, the screw nut 113, and the first bearing 146, but also includes a second bearing 142. A through hole is defined inside the screw rod 144 in the axial direction thereof. The proximal inner tube 126 passes through the through hole, and is in clearance fit with the through hole, so that the outer wall of the proximal inner tube 126 does not interfere with the inner wall of the screw rod 144 during the rotation of the screw rod 144. A second bearing 142 is sleeved over each of both ends of the proximal inner tube 126. The side of the second bearing 142 away from the screw rod 144 is provided with a retaining nut 141 for the inner tube. The retaining nut 141 is fastened to the proximal inner tube 126 by a screwed connection so as to limit the axial movement of the second bearing 142. The inner ring of the second bearing 142 is fixedly connected to the proximal inner tube 126, the outer ring of the second bearing 142 is fixed to the inner wall of the respective end of the screw rod 144. The inner ring of the first bearing 146 is sleeved over the proximal outer wall of the screw rod 144. The second bearing 142 is, for example, a deep groove ball bearing, and the first bearing 146 is, for example, an angular contact bearing. The screw nut 113 is fixedly connected to the outer tube assembly. Specifically, the screw nut 113 is fixedly connected to the proximal end A of the outer tube. The distal end of the housing 13 is fixedly connected to the proximal end B of the stabilizing tube.

In this embodiment, the outer ring of the first bearing 146 is fixedly connected to the housing 13, the inner ring of the first bearing 146 is fixedly connected to the outer wall of the proximal end of the screw rod 144, the outer rings of the second bearings 142 are respectively fixedly connected to the proximal inner wall of the screw rod 144 and the distal inner wall of the screw rod 144, and the inner rings of the second bearings 142 are fixedly connected to the proximal inner tube 126. As a result, the proximal inner tube 126 is restricted from moving in the axial direction, and the axial position of the screw rod 144 is fixed. Therefore, the screw rod 144 can rotate in the circumferential direction to drive the screw nut 113 to move axially, so that the entire outer tube assembly 11 is moved axially.

Figure 12:
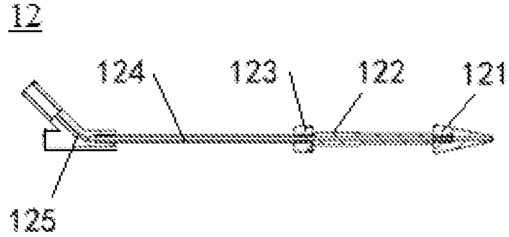
FIG. 12 is a schematic diagram showing the structure of a third exemplary inner tube assembly (excluding the proximal inner tube) according to an embodiment of the present invention.
Figure 13:
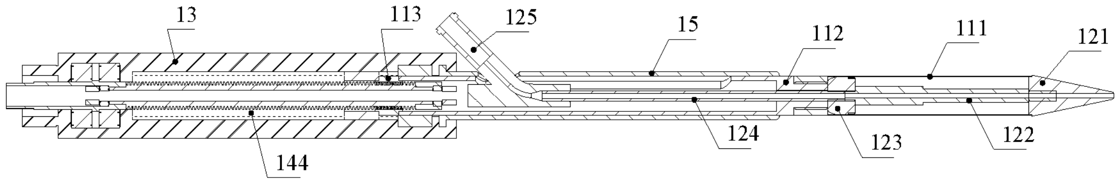
FIG. 13 is a cross-sectional view of a third exemplary catheter assembly according an embodiment of the present invention.

FIG. 12 is a schematic diagram showing the structure of a third exemplary inner tube assembly (excluding the proximal inner tube) according to an embodiment of the present invention. FIG. 13 is a cross-sectional view of a third exemplary catheter assembly according an embodiment of the present invention. In both the structures of the two exemplary inner tube assemblies shown in FIGS. 4 and 9, the proximal inner tube 126 is included. It should be noted that the inner tube assembly of the embodiment of the present invention may not include the proximal inner tube 126. As shown in FIGS. 12 and 13, the inner tube assembly 12 includes, along a direction from the distal end to the proximal end, a tapered head 121, a distal inner tube 122, a fastener 123, a middle inner tube 124, and a Luer connector 125 that are connected in sequence. The Luer connector 125 has a protruding end. The protruding end of the Luer connector 125 can be fixedly connected to the housing 13 or the second stabilizing tube 15, and thus the inner tube assembly 12 can be fixedly arranged due to the Luer connector 125. Specifically, the protruding end of the Luer connector 125 is fixedly connected to the proximal end of the second strip-shaped opening of the second stabilizing tube 15 by welding or adhesion. Alternatively, the protruding end of the Luer connector 125 is fixedly connected to the housing 13 by welding or snapping. This can be selected by those skilled in the art according to the actual situation.

Both the inner tube assemblies shown in FIGS. 9 and 12 include the Luer connector 125, and an outer tube assembly that matches the Luer connector 125 can be provided. Please refer to the description of the outer tube assembly in FIGS. 10 and 11 for details, as an example, a first strip-striped opening is defined on the second outer tube 112 of the outer tube assembly along the axial direction, and the protruding end of the Luer connector protrudes from the first strip-shaped opening, the detail description of which is omitted here.

Figure 14:
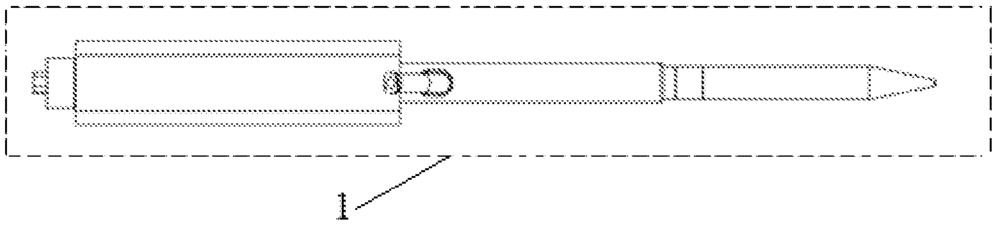
FIG. 14 is a schematic diagram of a second exemplary catheter assembly according an embodiment of the present invention.
Figure 15:
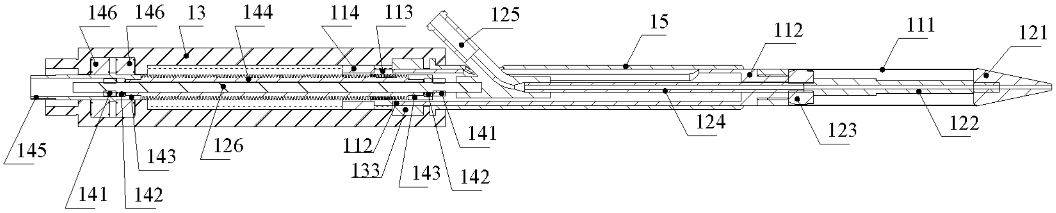
FIG. 15 is a cross-sectional view of FIG. 14.

FIG. 14 is a schematic diagram of a second exemplary catheter assembly according an embodiment of the present invention. FIG. 15 is a cross-sectional view of FIG. 14. As shown in FIGS. 13 and 15, both the second and third exemplary catheter assemblies include the second stabilizing tube 15 whose the proximal end is fixedly connected to the distal end of the housing 13. The second stabilizing tube 15 is sleeved over the second outer tube 112, and a second strip-shaped opening which is in positional correspondence with the first strip-shaped opening is defined on the second stabilizing tube 15. The protruding end of the Luer connector 125 protrudes from the second strip-shaped opening. The second stabilizing tube 15 supports the second outer tube 112 and also prevents the operator from directly contacting the outer tube assembly. The housing 13 and the second stabilizing tube 15 support the entire delivery device for medical implant, which not only facilitates the delivery by the delivery device, but also improves the release stability of the medical implant (e.g., a valve).

Figure 16:
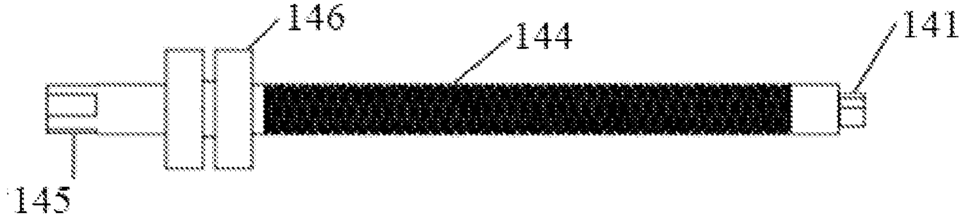
FIG. 16 is a front view of a transmission assembly according an embodiment of the present invention.
Figure 17:
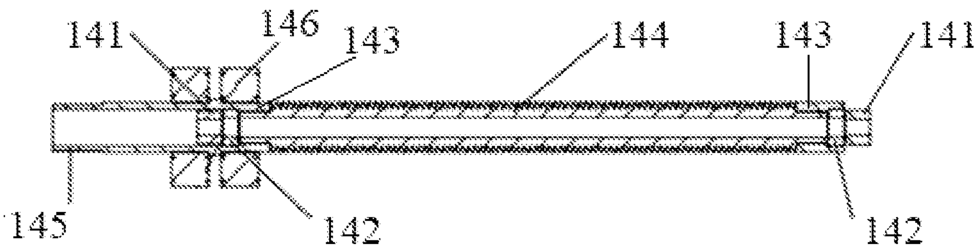
FIG. 17 is a cross-sectional diagram of the transmission assembly according an embodiment of the present invention.

FIG. 16 is a front view of a transmission assembly according an embodiment of the present invention. FIG. 17 is a cross-sectional diagram of the transmission assembly according an embodiment of the present invention. As shown in FIGS. 1, 3 and 15 to 17, the transmission assembly is configured to transmit movement. In particular, the transmission assembly receives the circumferential movement from the transmission shaft 2 and then converts it into an axial movement for the outer tube assembly 11. According to the embodiment, the space inside the screw rod 144 is utilized skillfully, thereby reducing the size of the catheter assembly 1 so that the catheter assembly 1 is more compact, which is more suitable for holding, moving, and positioning. Specifically, the screw rod 144 is threaded in the middle, and the two ends (i.e., the proximal end and the distal end) of the screw rod 144 are not threaded in order for connecting with bearings. The unthreaded part at both ends of the screw rod 144 can be formed integratedly or detachably with the threaded part in the middle of the screw rod. When the unthreaded part at both ends of the screw rod 144 is formed detachably with the threaded part in the middle of the screw rod, the unthreaded part at both ends (i.e., the proximal end and the distal end) of the screw rod 144 is for example a seat 143 for screw rod, the seat 143 is fixedly connected with the screw rod 144, the outer ring of the second bearing 142 is fixedly connected to the inner wall of the seat 143, the seat 143 at the proximal end is fixedly connected with the seat 145 for flexible shaft, for example by welding or adhesion. The other end of the seat 145 is used to connect with the transmission shaft 2 to receive the movement of the transmission shaft 2 and convert it into the self-rotating movement of the screw rod 144. The seat 145 and the seat 143 can be made separately or as an integrated structure. The seat 145 and the seat 143 can also be made integratedly with the threaded part in the middle of the screw rod 144. The inner ring of the first bearing 146 is sleeved and fixed on the proximal outer wall of the screw rod 144 (that is, the outer wall of the seat 145).

Specifically, the catheter assembly 1 further includes a circumferential stop piece 114 fixedly connected to the screw nut 113. The circumferential stop piece 114 cooperates with the housing 13 to form a structure which limits a circumferential position and allows an axial movement. In the catheter assembly 1, along a direction from the distal end to the proximal end, the sheath tube 111, the second outer tube 112, the screw nut 113, and the circumferential stop piece 114 are fixedly connected in sequence, and the screw nut 113 is engaged with the screw rod 144 so that the entire outer tube assembly 11 can be driven by the screw rod 144 to move axially. The circumferential stop piece 114 matching in shape with the inner surface of the housing 13 limits the freedom of rotation of the outer tube assembly 11, so that the outer tube assembly 11 and the housing 13 are circumferentially locked but axially movable with each other. The circumferential stop piece 114 and the screw nut 113 can be fixedly connected by welding or bonding, can be integrally formed, or can be connected separately.

Figure 18:
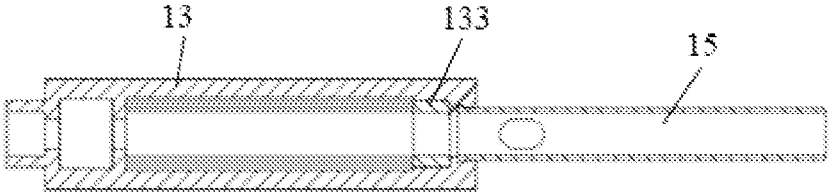
FIG. 18 is a schematic diagram showing the assembling of the housing with the stabilizing tube according an embodiment of the present invention.

FIG. 18 is a schematic diagram showing the assembling of the housing with the stabilizing tube according an embodiment of the present invention. As shown in FIGS. 2 to 7, the outer ring of the first bearing 146 is fixedly connected to the housing 13, the inner ring of the first bearing 146 is fixedly connected to the proximal outer wall of the screw rod 144, the outer rings of the second bearings 142 are fixedly connected the proximal inner wall and the distal inner wall of the screw rod 144, and the inner ring of the second bearing 142 is fixedly connected to the proximal inner tube 126. Therefore, the proximal inner tube 126 is restricted from moving in the axial direction. The distal end of the proximal inner tube 126 is fixedly connected to the proximal end of the Luer connector 125. The protruding end of the Luer connector 125 protrudes from the first strip-shaped opening of the second outer tube 112 and the second strip-shaped opening of the second stabilizing tube 15, locking the proximal inner tube 126 and the middle inner tube 124 so that they cannot be rotated circumferentially. As a result, both the axial and circumferential directions of the proximal inner tube 126 are restricted, thereby restricting the six degrees of freedom of the inner tube assembly 12 for fixing medical implants (such as valve stents).

Further, the housing 13 further includes a housing lining 133 fixedly connected inside the housing 13. The housing lining 133 is sleeved over the second outer tube 112. The housing lining 133 is preferably made of a low-friction material. The housing lining 133 is beneficial to ensuring the stability of the second outer tube 112 and a reduced frictional resistance during its axial movement. In an aspect, the second outer tube 112 is in close contact with the housing lining 133, which further limits the radial movement of the second outer tube 112, and in another aspect, it can also prevent the second outer tube 112 from being worn out.

Figure 19:
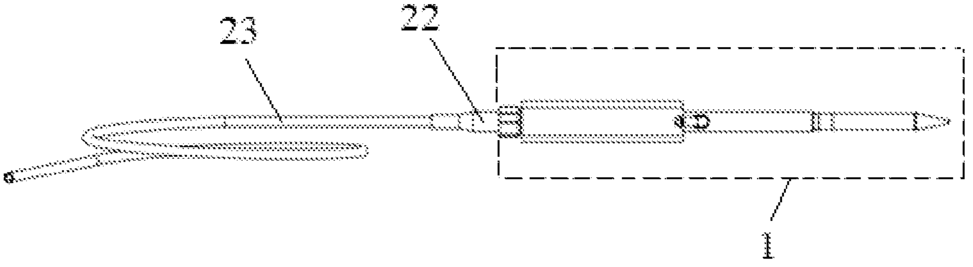
FIG. 19 is a schematic diagram showing the assembling of the catheter assembly with the transmission shaft according an embodiment of the present invention.
Figure 20:
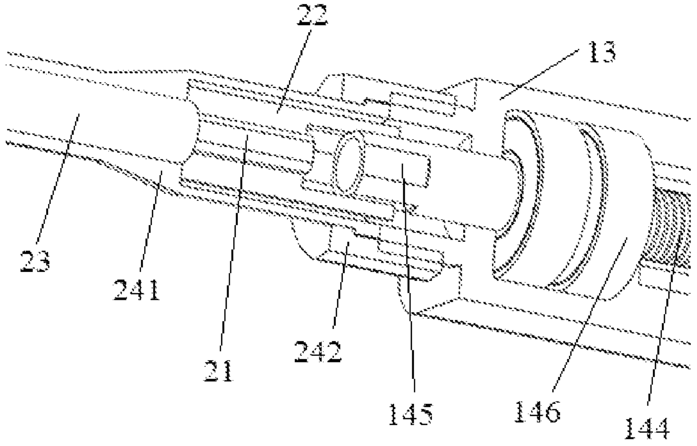
FIG. 20 is a perspective view partially showing the cross section of a structure where the catheter assembly is connected with the transmission shaft as shown in FIG. 19.
Figure 21:
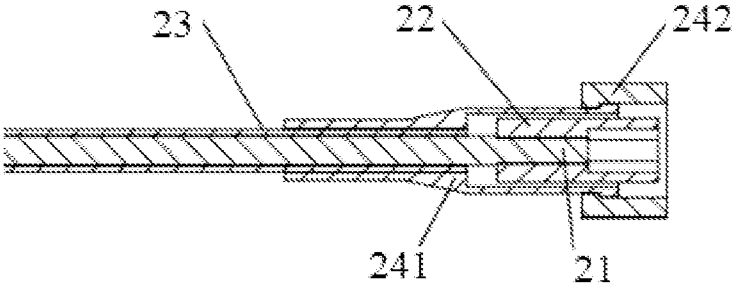
FIG. 21 is a plan view partially showing the cross section of a structure where the catheter assembly is connected with the transmission shaft as shown in FIG. 19.

FIG. 19 is a schematic diagram showing the assembling of the catheter assembly with the transmission shaft according an embodiment of the present invention. FIG. 20 is a perspective view partially showing the cross section of a structure where the catheter assembly is connected with the transmission shaft as shown in FIG. 19. FIG. 21 is a plan view partially showing the cross section of a structure where the catheter assembly is connected with the transmission shaft as shown in FIG. 19. As shown in FIGS. 1 and 19 to 21, the transmission shaft 2 is configured to transmit the driving force of the handle 3, and transmits the movement signal sent from the handle 3 to the catheter assembly 1. The transmission shaft 2 includes a flexible transmission shaft, which can be wound, and thus the overall size of the packaged delivery device can be reduced and also the space occupied during surgery can be reduced. The transmission shaft 2 further includes a connector 22 and an outer tube 23 for flexible transmission shaft. The flexible transmission shaft 21 is an elastic shaft with low rigidity and is freely bendable for transmission. It is used to connect two shafts with different axes and not in a same direction or with relative motion so as to transmit rotational motion and torque. It can flexibly transfer rotational motion and torque. In this embodiment, the length of the flexible transmission shaft 21 can be designed according to actual needs, and it can transmit circumferential motion regardless of its length. More preferably, it can rotate in the forward and reverse directions. It can be solid or hollowed. Exemplarily, the flexible transmission shaft 21 has the following characteristics: it has a 2-4 layer spiral structure, more preferably a double layer spiral structure with opposite spiral directions and having no pitch, where the single spiral material is a filament or a wire; it is made of metal material, such as stainless steel, nickel-titanium alloy and the like; the spiral structure has an outer diameter greater than or equal to 0.1 mm, more preferably, greater than or equal to 4 mm, so as to match the size of the transmission assembly 14, to reduce the energy loss as much as possible during the transmission process.

The connector 22 is used to connect the flexible transmission shaft 21 with the seat 145 of the transmission assembly 14, more preferably in a detachable manner. The flexible transmission shaft 21 is arranged in the outer tube 23 so that the outer tube 23 can protect the flexible transmission shaft 21 and makes it is convenient for the operator to grasp.

Please continue to refer to FIGS. 1 and 19 to 21, the transmission shaft 2 and the catheter assembly 1 is detachably connected. For example, the connector 22 and the seat 145 can be connected in a snap-fit manner. In this case, one end of the connector 22 is connected to the flexible transmission shaft 21, and the other end of the connector 22 is connected with the seat 145. The connection between the connector 22 and the flexible transmission shaft 21 can be achieved by any one or a combination of two or more of snap-fit, bonding or welding. In order to facilitate processing and assembling, for example, it can be achieved by snap-fit. In this case, the flexible transmission shaft 21 has a structure with a non-circular surface at its distal end, and the connector 22 has an inner surface of a corresponding shape, so that the two is fixedly connected by snap-fit. The connection between the connector 22 and the seat 145 is preferably in a detachable manner, more preferably a snap-fit manner. In this case, the distal end of the connector 22 has an inner surface that matches the outer surface of the seat 145 in shape, to form a snap-fit therebetween, so that the seat 145 can be snapped into the distal end of the connector 22 when a connection therebetween is required.

In order to further limit the axial displacement of the transmission shaft 2 relative to the catheter assembly 1 and improve the robustness of the device, the transmission shaft 2 also includes a fastener assembly, which includes a first fastener 241 connected to the outer tube 23, and a second fastener 242 connected to the housing 132. The second fastener 242 is connected to the housing 132 by means of threads, snap-in grooves, and the like. The second fastener 242, the first fastener 241, and the outer tube 23 are connected in sequence and sleeved over the surface of the flexible transmission shaft 21.

Figure 22:
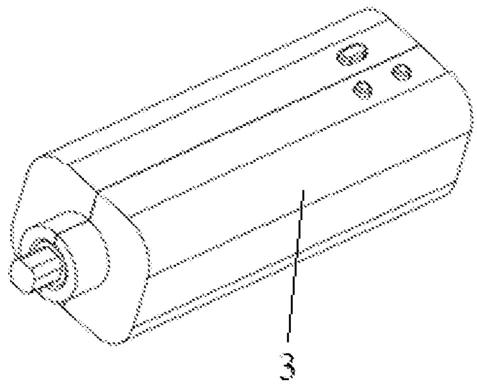
FIG. 22 is a schematic diagram showing a handle according to an embodiment of the present invention.
Figure 23:
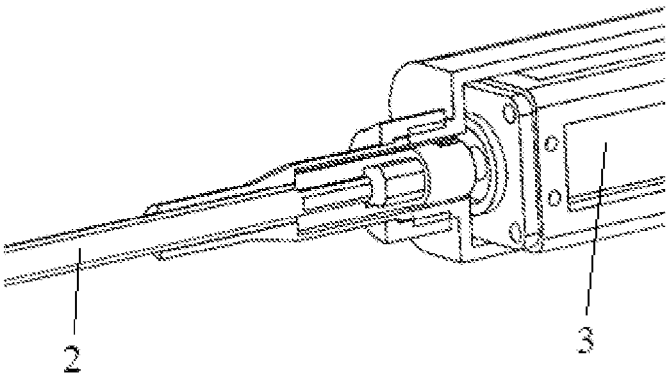
FIG. 23 is a perspective view partially showing the cross section of a structure where the handle is assembled with the transmission shaft according to an embodiment of the present invention.

FIG. 22 is a schematic diagram showing a handle according to an embodiment of the present invention. FIG. 23 is a perspective view partially showing the cross section of a structure where the handle is assembled with the transmission shaft according to an embodiment of the present invention. As shown in FIGS. 1 and 20 to 23, the handle 3 according to the embodiment of the present invention may be operated manually, electrically, or the combination thereof. Taking a handle operated electrically as an example, as shown in FIG. 22, a driving mechanism is provided inside the handle 3. The driving mechanism is connected with the transmission shaft 2 to drive the transmission shaft 2 to move circumferentially, and the transmission shaft 2 transmits the rotational torque to the transmission assembly 14 in the catheter assembly 1, so that the entire outer tube assembly 11 is driven to move axially for loading and releasing the medical implant. In the embodiment of the present invention, the handle 3 is operated manually or electrically to generate circumferential driving force, the transmission shaft 2 transmits the circumferential rotation angle in a certain length of the flexible transmission shaft at a ratio of 1:1, and the rotation torque is transmitted to the catheter assembly 1 at a ratio of 1:1. The ability of the catheter assembly 1 to convert circumferential rotation into axial movement realizes the separation of driving force from moving parts. The handle 3 and the transmission shaft 2 may be fixedly connected or detachably connected.

This embodiment discloses a delivery device for medical implants. The delivery device can solve the problem that the delivery and positioning of medical implants (such as interventional valves) is not flexible enough, help to effectively position medical implants (such as interventional valves) in the body, improve the accuracy of the operation, and also shorten the operation time and improve the quality of the operation. The handle is operated manually or electrically to drive the bearing to force the movable parts of the flexible shaft to rotate, so that the screw rod drives the outer tube and the sheath tube to move axially relative to the inner tube assembly to realize the treatment (e.g., loading and releasing) of medical implants (such as valve stents), which will be described in the following parts. The transmission shaft 2 and the handle 3 are always in connection with each other in the following stages.

Valve loading process: connect the transmission shaft 2 with the catheter assembly 1, specifically connect the connector 22 with the seat 145, drive the handle 3 so that the transmission shaft 2 drives the screw rod 144, and the second outer tube 112 and the sheath tube 111 moves toward the proximal end until the fastener 123 is exposed form the groove. Then, the two lugs of a medical implant (such as a self-expanding valve stent) are stuck in the groove, the stent is stabilized with the aid of an auxiliary loading tool, and the second outer tube 112 is driven to move distally, and the valve stent is pressed and held. Until the sheath tube 111 completely wraps the valve stent, the loading of the valve stent is completed, and then the transmission shaft 2 and the catheter assembly 1 are disassembled, so that the catheter assembly 1 is separated from the transmission shaft 2.

Valve delivery process: move the distal end of the separated catheter assembly 1 into human body through the puncture point along the guide wire. The distal part of the catheter assembly 1 is then delivered to the lesion location long the transapical passageway and adjusted to be with a suitable angle.

Valve release process: connect the transmission shaft 2 to the catheter assembly 1, and after reconfirming the angle of the sheath tube 111, drive the handle 3 so that the transmission shaft 2 drives the screw rod 144, thereby moving the second outer tube 112 and the sheath tube 111 proximally, start to release the valve stent until the valve stent is completely released at the designated position and is out of the delivery system. Specifically, as the sheath tube 111 moves proximally, the valve stent is slowly released until the distal end of the sheath tube 111 moves to the fastener 123 to expose the groove where the fastener 123 is, and thus the valve stent is completely released.

The delivery system retrieval process: the transmission shaft 2 and the catheter assembly 1 are still connected, and the gap between the sheath tube 111 and the tapered head 121 is closed. Then control the handle 3, withdraw the catheter assembly 1 to leave the human body through the transapical passageway from the puncture point thereof.

The embodiment of the present invention describes the delivery and release process of the valve. Those skilled in the art can understand that the release and retrieval device disclosed in the present invention is not only used for the delivery of heart valves, but also can be used for the delivery of other valves. The present invention is not limited to one way of delivering heart valves.

In summary, the delivery device for medical implants has a detachable structure and includes a handle and a catheter assembly that are separated from each other. The catheter assembly of the delivery device has less weight than that of a traditional delivery device, so that the operator can position the medical implant and adjust the position of the medical implant by moving only the catheter assembly. Compared with the traditional delivery system which is only allowed to be moved integrally, the catheter assembly is lighter in weight and smaller in size, and can be moved more conveniently and flexibly. It is thus more conducive to the positioning and the fine-tuning of the position during the operation, and improves the stability, precision and accuracy of the operation. A high-quality implantation of medical implants can be achieved. Moreover, the impact of vibration and/or movement of the handle on the catheter assembly are avoided, which further improves the stability and thus the quality of the operation.

The transmission shaft and the catheter assembly are detachably connected, which improves the convenience in the process of loading, transporting and releasing the medical implant, and the detachable connection also improves the convenience of packaging and transportation.

The transmission shaft is flexible and can be wound so that the overall size of the packaged delivery device can be reduced and also the space occupied during surgery can be reduced. A through hole is defined in the screw rod in the axial direction, and the proximal inner tube passes through the through hole. Therefore, the space inside the screw rod is utilized skillfully, thereby reducing the size of the catheter assembly so that the catheter assembly is more compact, which makes it more suitable for holding, moving, and positioning.

Compared with a rigid straight tube based delivery device (with or without a holder), the present embodiment can achieve sensitive and effective adjustment in the positioning ability of the conveying device. The delivery device provided in this embodiment can realize the accurate release of the medical implant (e.g., the prosthetic valve) at the diseased location, ensure the quality of the release process, and shorten the operation time.

It is noted that the embodiments disclosed herein are described in a progressive manner, with the description of each embodiment focusing on its differences from other embodiments. Reference can be made between the embodiments for their identical or similar parts. As to the methods provided in the embodiments of the present invention, they are described in a simple way because they correspond to the device described in the embodiments of the present invention. Therefore, reference can be made to the description of the device for details.

The above description is only for the description of preferred embodiments of the present invention, and is not intended to limit the scope of the present invention. Any changes and modifications made by those skilled in the art according to the above disclosure are all within the protection scope of the appended claims.

What is claimed is:

1. A delivery device for medical implants, wherein the delivery device has a detachable structure and includes a handle and a catheter assembly that are separated from each other, and the handle and the catheter assembly are connected by a transmission shaft, wherein the catheter assembly comprises an inner tube assembly and an outer tube assembly sleeved over the inner tube assembly, and wherein the handle is configured to drive the transmission shaft to rotate to axially move the outer tube assembly relative to the inner tube assembly, wherein the catheter assembly further comprises a transmission assembly, the transmission assembly comprising a screw rod and a screw nut, wherein the screw rod is engaged with the screw nut that is fixedly connected to the outer tube assembly; when the transmission shaft is connected to the catheter assembly, the transmission shaft is connected to the screw rod so that the screw nut and the outer tube assembly are forced to move axially resulting from rotation of the screw rod due to rotation of the transmission shaft, and wherein the catheter assembly further comprises a housing, and the transmission assembly further comprises a first bearing, and wherein an outer ring of the first bearing is embedded in and fixedly connected to a proximal end of the housing, and an inner ring of the first bearing is sleeved over and fixedly connected to a proximal end of the screw rod.

2. The delivery device for medical implants according to claim 1, wherein the transmission shaft is detachably connected to the catheter assembly.

3. The delivery device for medical implants according to claim 1, wherein the inner tube assembly comprises a tapered head, a distal inner tube, a fastener and a proximal inner tube that are sequentially connected along a direction from a distal end to a proximal end.

4. The delivery device for medical implants according to claim 3, wherein the outer tube assembly comprises a sheath tube and a first outer tube connected to a proximal end of the sheath tube, and wherein the first outer tube has a proximal end fixedly connected to the screw nut.

5. The delivery device for medical implants according to claim 4, wherein the first outer tube has an inner wall where a circumferential stopper is provided, and an outer wall of the proximal inner tube matches with the circumferential stopper so that the proximal inner tube is restricted from rotating circumferentially.

6. The delivery device for medical implants according to claim 5, wherein the catheter assembly further comprises a first stabilizing tube having a proximal end fixedly connected to a distal end of the housing, and wherein the first stabilizing tube is sleeved over the first outer tube.

7. The delivery device for medical implants according to claim 3, wherein the inner tube assembly further comprises an intermediate inner tube and a Luer connector having a protruding end, and wherein the tapered head, the distal inner tube, the fastener, the intermediate inner tube, the Luer connector, and the proximal inner tube are sequentially connected along a direction from a distal end to a proximal end.

8. The delivery device for medical implants according to claim 7, wherein the outer tube assembly comprises a sheath tube and a second outer tube connected to a proximal end of the sheath tube, and wherein a proximal end of the second outer tube is fixedly connected to the screw nut; a first strip-shaped opening is axially defined on the second outer tube, and the protruding end of the Luer connector protrudes from the first strip-shaped opening.

9. The delivery device for medical implants according to claim 8, wherein the catheter assembly further comprises a second stabilizing tube having a proximal end fixedly connected to a distal end of the housing, the second stabilizing tube is sleeved over the second outer tube, a second strip-shaped opening is axially defined on the second stabilizing tube, and the second strip-shaped opening is in positional correspondence with the first strip-shaped opening, the protruding end of the Luer connector protrudes from the first strip-shaped opening and then protrudes from the second strip-shaped opening.

10. The delivery device for medical implants according to claim 3, wherein the transmission assembly further comprises two second bearings, and wherein a through hole is formed axially in the screw rod, and the proximal inner tube passes through and is in clearance fit with the through hole, each of the second bearings is sleeved over a respective one of two ends of the proximal inner tube, an outer ring of each of the second bearings is fixedly connected to an inner wall of a respective end of the screw rod, and an inner ring of the first bearing is sleeved over and fixedly connected to a proximal outer wall of the screw rod.

11. The delivery device for medical implants according to claim 1, wherein the inner tube assembly comprises, along a direction from a distal end to a proximal end, a tapered head, a distal inner tube, a fastener, and a middle inner tube and a Luer connector having a protruding end.

12. The delivery device for medical implants according to claim 1, wherein the catheter assembly further comprises a circumferential stop piece fixedly connected to the screw nut, and wherein the circumferential stop piece cooperates with the housing so that the outer tube assembly and the housing are circumferentially locked and axially movable.

13. The delivery device for medical implants according to claim 1, wherein the transmission shaft comprises a flexible transmission shaft.

14. The delivery device for medical implants according to claim 13, wherein the flexible transmission shaft has 2 to 4 layers of spiral structure, each of which has an outer diameter greater than or equal to 0.1 mm, and the flexible transmission shaft is made of metal.

15. The delivery device for medical implants according to claim 13, wherein the transmission shaft further comprises a connector and an outer tube for the flexible transmission shaft, and wherein the outer tube for the flexible transmission shaft is sleeved over the flexible transmission shaft, and the flexible transmission shaft is connected to the catheter assembly by the connector.

16. The delivery device for medical implants according to claim 1, wherein the transmission shaft is fixedly connected to the catheter assembly.

* * * * *